US009415911B2

(12) United States Patent
Schaefer (10) Patent No.: US 9,415,911 B2
(45) Date of Patent: Aug. 16, 2016

(54) LID APPARATUS FOR THE PIVOTABLE SUPPORT OF A LID ON A MEDICAL DEVICE FOR EXTRACORPOREAL BLOOD TREATMENT; MEDICAL DEVICE FOR EXTRACORPOREAL BLOOD TREATMENT WITH LID APPARATUS (71) Applicant: B. Braun Avitum AG, Melsungen (DE)

(72) Inventor: Oliver Schaefer, Neuenstein (DE)

(73) Assignee: B. BRAUN AVITUM AG, Melsungen (DE)

( * ) Notice: Subject to any disclaimer, the term of this patent is extended or adjusted under 35 U.S.C. 154(b) by 474 days.

(21) Appl. No.: 13/927,773

(22) Filed: Jun. 26, 2013

(65) Prior Publication Data
US 2014/0003985 A1   Jan. 2, 2014

(30) Foreign Application Priority Data

Jun. 27, 2012   (DE) .......................... 10 2012 105 614

(51) Int. Cl.
F04B 43/08    (2006.01)
B65D 51/00   (2006.01)
(Continued)

(52) U.S. Cl.
CPC ............... *B65D 51/00* (2013.01); *F04B 43/08* (2013.01); *F04B 43/12* (2013.01); *E05D 11/1064* (2013.01)

(58) Field of Classification Search
CPC .......... F04B 45/06; F04B 45/08; F04B 43/08; F04B 43/12; Y10T 16/5323; Y10T 16/53822; Y10T 16/5383; B65D 51/00; E05D 11/1064
USPC ........................................................... 16/281
See application file for complete search history.

(56) References Cited

U.S. PATENT DOCUMENTS 663,571 A * 12/1900 Hawgood .................. E05D 3/00
                                                                  16/281
(Continued)

FOREIGN PATENT DOCUMENTS

DE    18 75 008    7/1963
DE    84 25 352    8/1984
(Continued)

OTHER PUBLICATIONS

German Search Report for DE 10 2012 105 614.5 issued Mar. 7, 2013.
(Continued)

*Primary Examiner* — Charles Freay
*Assistant Examiner* — Philip Stimpert
(74) *Attorney, Agent, or Firm* — RatnerPrestia (57) ABSTRACT A lid apparatus for a medical device for extracorporeal blood treatment that includes a lid which is hinged by means of at least one pivot joint at the medical device is disclosed. The pivot joint includes thereby a first joint section which may be positioned at the lid, and a second joint section which may be connectable to the medical device, wherein the joint sections are pivotable about a pivot axis at least between a first position, in which the lid is open, and a second position, in which the lid covers at least a part of the medical device, wherein also the joint sections are latchable in at least one pivoting position. The lid apparatus includes at least one pair of contact surfaces which are perpendicular to the axis of rotation and resiliently biased against each other, wherein at least one of the contact surfaces includes a rolling and latching geometry which is configured such that the lid latches in the second position and the pivoting moveability of the pivot joint is only released when the resilient biasing force is overcome. A medical device for extracorporeal blood treatment including a peristaltic pump and such a lid apparatus is also disclosed.

10 Claims, 7 Drawing Sheets (51) Int. Cl.
*F04B 43/12* (2006.01)
*E05D 11/10* (2006.01)

(56) References Cited

U.S. PATENT DOCUMENTS

| | | | |
|---|---|---|---|
| 5,928,177 A | * | 7/1999 | Brugger .................. A61M 1/10 604/6.11 |
| 7,547,200 B2 | | 6/2009 | O'Mahony et al. |
| 2009/0129944 A1 | | 5/2009 | Stemple et al. |
| 2010/0129247 A1 | | 5/2010 | Lauer |

FOREIGN PATENT DOCUMENTS

| | | | |
|---|---|---|---|
| DE | 10 2007 020 573 | | 11/2008 |
| EP | 0 019 205 | | 11/1980 |
| EP | 0 085 874 | | 8/1983 |
| GB | 0007534 | * | 3/1913 |
| GB | 07534 A | | 3/1914 |
| JP | 2008 190333 | | 8/2008 |

OTHER PUBLICATIONS

European Search Report for EP 13173340.4 dated Oct. 10, 2013.

* cited by examiner

LID APPARATUS FOR THE PIVOTABLE SUPPORT OF A LID ON A MEDICAL DEVICE FOR EXTRACORPOREAL BLOOD TREATMENT; MEDICAL DEVICE FOR EXTRACORPOREAL BLOOD TREATMENT WITH LID APPARATUS

CROSS REFERENCE TO RELATED APPLICATIONS

This application claims priority to German Patent Application No. DE 10 2012 105 614.5 filed Jun. 27, 2012, the contents of such application being incorporated by reference herein.

FIELD OF THE INVENTION

The invention relates to a lid apparatus for a medical device for extracorporeal blood treatment, comprising a lid and a second component, wherein the second component is part of the medical device and the lid is pivotably mounted on the second component and is configured to cover the second component in a closed position at least partially, wherein the lid is latchable with respect to the second component in at least one position. The invention further relates to a medical device for extracorporeal blood treatment comprising such a lid apparatus.

BACKGROUND INFORMATION

In medical devices for extracorporeal blood treatment (Dialysis), peristaltic pumps are often used which supply the blood removed from the patient to a dialyzer and return the blood to the patient. Such pumps operate peristaltically, wherein a tube segment in the form of a loop lies on a correspondingly curved running surface. In that case, a pump's rotor lying inside the running surface moves with its outer edges along the tube segment, whereby it presses locally on the tube and thus, together with the elastic material properties of the tube segment, it allows a blood supply through the tube segment. Therefore the blood is introduced into the tube segment via a first connection and conducted away via a further connection at the other end of the tube segment. Thus for example the tube segment forms, together with the supply and discharge lines and the plurality of air traps, a so-called transfer system, with which the blood of the patient is supplied to a dialyzer and then supplied back to the patient.

DESCRIPTION OF THE RELATED ART

For example published patent application document DE 10 2007 020 573 A1 discloses such a peristaltic pump with a stator, a rotor and a rotor drive, by which a tube is inserted between the rotor and the tube roller track of the stator. The tube is pressed against the tube roller track of the stator by means of the rotation of the rotor together with the circulating motion of tube rollers, whereby fluid is pumped through the tube.

Patent document U.S. Pat. No. 7,547,200 B2 also discloses such a peristaltic pump with a rotor and rollers wherein said rollers press an inserted tube against a semicircular tube roller track. Here the roller track has a chamfered edge at one end to receive the tube which is attached to an interchangeable insert.

The transfer systems used for such pumps in the medical technical field are usually exchanged after every treatment and are not reused for another patient. Thus a used tube segment must be removed from the pump before a new transfer system is introduced into the device. Therefore the associated lid and peristaltic pump are operated at least four times per treatment, in order to set up and dismantle again the transfer system on the medical device.

Usually the employed lid comprises at least one hinge about which the lid is pivotable between an open and a closed position. In order to support the handling of the lid, it is further known to provide various holding or latching positions. For example the closed position of the lid can be defined as a position in which the lid is held by means of a magnetic force at the pump housing. To this end, a magnet installed in the lid or pump housing interacts with a ferromagnetic material installed into the lid or pump housing.

A known technical solution for a latching function in a defined opening angle consists of stationary pivots in combination with a supporting element which may be formed, for example, by a sprung plunger which applies a defined force onto a level surface of the lid. However the arrangement of the supporting elements in such systems can be unfavourable, in particular when a spring loaded plunger engages on a centrally positioned functional surface of the typically transparent plastic lid. Through such an arrangement, the system generates high loads on the lid, which can lead to negative signs of wear at the point of force application.

SUMMARY OF THE INVENTION

An object of aspects of the invention is therefore to provide a lid apparatus for a medical device for extracorporeal blood treatment with which a lid is latchable in at least one position with respect to a component of the medical device, wherein the lid apparatus is easy to assemble and leads to the minimum possible signs of wear during service.

A further object of aspects of the invention is to provide a medical device for extracorporeal blood treatment comprising such a lid apparatus, wherein the lid apparatus is to be suited in particular to cover a peristaltic pump of a medical device for extracorporeal blood treatment.

The lid apparatus according to aspects of the invention for a medical device for extracorporeal blood treatment comprises a lid which is hinged at the medical device via at least one pivot joint. In this way, the pivot joint comprises a first joint section and a second joint section. The joint sections are pivotable with respect to each other about an axis of rotation at least between a first position in which the lid is open, and a second position, in which the lid covers at least a part of the medical device, and are releasably lockable or latchable in at least one pivoting position.

The first joint section may be positioned at the lid, and the second joint section may be connectable to the medical device.

The lid apparatus further comprises at least one pair of contact surfaces which, perpendicular to the axis of rotation, are resiliently biased against each other, wherein at least one of the contact surfaces comprises a rolling and latching geometry which is configured such that the lid latches in the second position, and the pivoting moveability of the pivot joint is only released when the resilient biasing force is overcome.

By means of the resilient biasing load, it is achieved that the contact surfaces of the lid apparatus always press against each other or roll or unload against each other during the relative rotation of the joint sections. The pivot point of the pivot joint changes by means of the rolling and latching geometry relative to the medical device or lid. In the second, or latched, position the latching geometry, e.g. a flattened portion, comes into contact with the contact surface at the other component, whereby the relative distance of the pivot axis shortens with the aid of the spring biasing load. In order to bring the pivot joint from the latched position back into a non-latched, or pivoting, position, i.e. in order to bring the rolling geometry, e.g. a circular arced surface, into contact with the contact surface on the other component and thus to increase again the relative distance of the pivot axis, the applied resilient biasing load must be overcome. If this predetermined force is not applied, the lid remains independently in the latched position.

According to aspects of the invention, the medical device may comprise a housing section with at least one retention system which includes a lid support as the second joint section, which is movable with respect to the medical device under the load of a spring. The lid is pivotably mounted about an axis of rotation at said lid support, wherein a pulling force can be applied to the lid by the spring loaded lid support. The contact surface comprising the rolling and latching geometry may be configured at the first joint section positioned at the lid. The rolling and latching geometry may include a latching surface, or flattened portion, and at least one convex rolling curve, wherein the rolling curve borders on the latching surface on one side. In the latched position of the lid, the latching surface contacts the other contact surface of the pair of contact surfaces, while the rolling curve slides, upon pivoting of the lid, from the latched position along the other contact surface of the pair of contact surfaces.

The latching surface is configured with respect to the rolling curve such that the lid, after passing through the rolling curve, latches on the latching surface. Here the latching surface may itself be formed in different ways. For example, this may involve a planar surface, or the latching surface may comprise a waved or jagged outer surface. In particular a concave latching surface has proved to be advantageous here.

The latched position of the lid may involve an opened or closed position of the lid relative to the medical device. For example the lid is latchable in the opened position in order to allow an operator access to the medical device, without the lid being able to pivot back by itself to the closed position, because this could, where appropriate, disturb actions of the operator at the second component. In this embodiment, the lid in the latched position does not therefore cover the medical device. However there are also conceivable applications in which a lid is to be latched in a closed position so that it does not open accidentally.

The latching is essentially caused by the pulling force which may constantly pull the lid support, and with it also the rolling and latching geometry, against the second component. In the latched position, the latching surface of the rolling and latching geometry bears on the second component and the lid can only be pivoted by a defined force from this latched position, because the spring force must be overcome in order to rotate the rolling and latching geometry such that a convex rolling surface can now slide on the other contact surface of the pair of contact surfaces. Depending on the shape of the rolling and latching geometry, it may also be achieved that the lid is secured in this second position as well.

In an exemplary embodiment of the invention, the retention system includes a plain bearing bush within which the lid support is axially movably mounted, wherein the plain bearing bush is fixed in a housing section of the medical device. The retention system can easily be pressed via the plain bearing bush, for example, into a hole in the housing section. In this way, in one embodiment of the invention, the lid support is cylindrically shaped, which brings with it the advantage that it is also movable in the circumferential direction inside the plain bearing bush. This simplifies in particular the assembly of the retention system because it does not have to be aligned to the housing section. Rather, the plain bearing bush with the lid support located inside it can be easily mounted in a hole in the housing section and the lid support can then be rotated inside the mounted plain bearing bush such that the lid can be attached to it. In order to simplify the connection of the lid with the lid support, it may however be provided that the lid support is formed to be plate-shaped in the region of the bearing for the lid. Thus for example it can be inserted into a corresponding hole with a rectangular cross section, whereby an orientation of the lid support in the lid in the circumferential direction can be realised. By means of this defined orientation, the insertion of a hinge pin through a hole in the lid support, for example, is simplified.

In an embodiment of the invention, the lid support protrudes with two ends lying opposite each other from the plain bearing bush, wherein a bearing for the lid is configured at one end, while at the other end the lid support comprises a stop, and the retention system further includes a compression spring which surrounds the lid support and is biased between the stop and the plain bearing bush. Through this construction of the retention system, the pull force on the lid can be realised, since the biased compression spring pushes the stop away from the plain bearing bush, whereby on the other side, the bearing of the lid support and with it the attached lid are constantly pulled in the direction of the plain bearing bush. However the pull force on the lid support may also be created by other spring loaded constructions.

In one embodiment, the other contact surface of the pair of contact surfaces may be formed by the outer surface of the housing section of the medical device. In that case, the latching surface, in the latched position of the lid, lies on the outer surface and the at least one rolling curve slides, upon pivoting of the lid, from the latched position along the outer surface.

The dimensions of the rolling and latching geometry and of the retention system may be chosen such that the latching surface in the latched position of the lid bears on the plain bearing bush, and the at least one rolling curve slides, upon pivoting of the lid, from the latched position along the plain bearing bush. In other words, the rolling and latching geometry at a joint section on one side and the abutting face of the plain bearing bush on the other side form a pair of contact surfaces which are resiliently biased against each other. This has the advantage that signs of wear do not occur on the material of the housing section, since stress and friction by the lid act only on the retention system and not on the material of the housing section. To this end, the material of the plain bearing bush may for example be chosen such that it resists this stress without impairment. In particular the plain bearing bush may be formed from a more resistant material than the housing section itself, which can simplify the design of components, for which the lid apparatus according to the invention is used.

However it may also be provided that the latching surface, in the latched position of the lid, bears at least partly on the housing, and that the at least one rolling curve slides, upon pivoting of the lid, from the latched position at least partly along the housing.

In a further embodiment of the invention, the rolling and latching geometry may comprise two convex rolling curves which border the latching surface on opposite lying sides. Thus an overload protection may be achieved in the latched position because, upon pivoting of the lid over the latched position, the rolling and latching geometry rolls onto the other contact surface in a controlled manner without damage arising. Such pivoting is made difficult by the spring force, but is not impossible, such that for example an unintentional pivoting of the lid does not lead to fracture or bending of components.

An edge may be configured between the at least one rolling curve and the latching surface. The latching surface therefore does not pass evenly into the rolling curve, rather an edge must first be overcome upon pivoting out of the latched position.

The lid may for example be mounted to the lid support by a hinge connection. In this way a hinge hole may be provided in the lid, through which the axis of rotation passes. In that case at least one second hole passes transversely through this hinge hole, wherein the lid support is inserted in the second hole such that a pin support of the lid support lies inside the hinge hole and is penetrated by a hinge pin which is inserted in the hinge hole. The hinge pin connects the lid and the lid support via a clearance fit, which allows an easy assembly and also makes the service at the lid apparatus very easy.

The hinge pin may thereby be axially fixed inside the hinge hole in order to ensure it against falling out. This may for example be realised by means of a circumferential groove on the hinge pin, in which a raised portion in the lid engages into the end of the hinge pin inside the associated hinge hole. However other types of latching geometries may also be provided wherein the constantly applied spring force which acts transversely to the hinge pin, supports the axial fixing of the hinge pin.

In addition, the lid may be attached to the medical device with one or more retention systems. For example at least two retention systems may be provided which pivotably mount a lid on two sides.

The invention also includes a medical device for extracorporeal blood treatment comprising such a lid apparatus. The lid apparatus according to the invention is also suited for the covering of various components of a medical device for extracorporeal blood treatment, wherein a lid is to be held in a certain position with respect to a component. In particular, the lid apparatus has proven to be advantageous for components which require a repeated manual actuation but are to be protected from external influence between the actuation phases. This is the case in peristaltic pumps in dialysis machines for example, because here single-use tube segments must be repeatedly installed and removed.

In an embodiment of the invention, a medical device for extracorporeal blood treatment includes at least one peristaltic pump having a pump housing which comprises a curved running surface and a rotor that rotates inside the running surface, wherein a tube segment of an extracorporeal blood circuit is introduceable between the running surface and the rotor. The peristaltic pump includes in addition a lid apparatus according to the invention, wherein the pump housing in the closed position is at least partially coverable by the lid.

In addition the latching can, for example, also be used to hold the lid in an open position such that an operator has access to the pump housing and can set up or dismantle the rotor and/or a tube segment, without the lid accidentally pivoting back into its closed position. In this way in particular the requirements for a one-hand operation for inserting and removing the transfer system are fulfilled.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
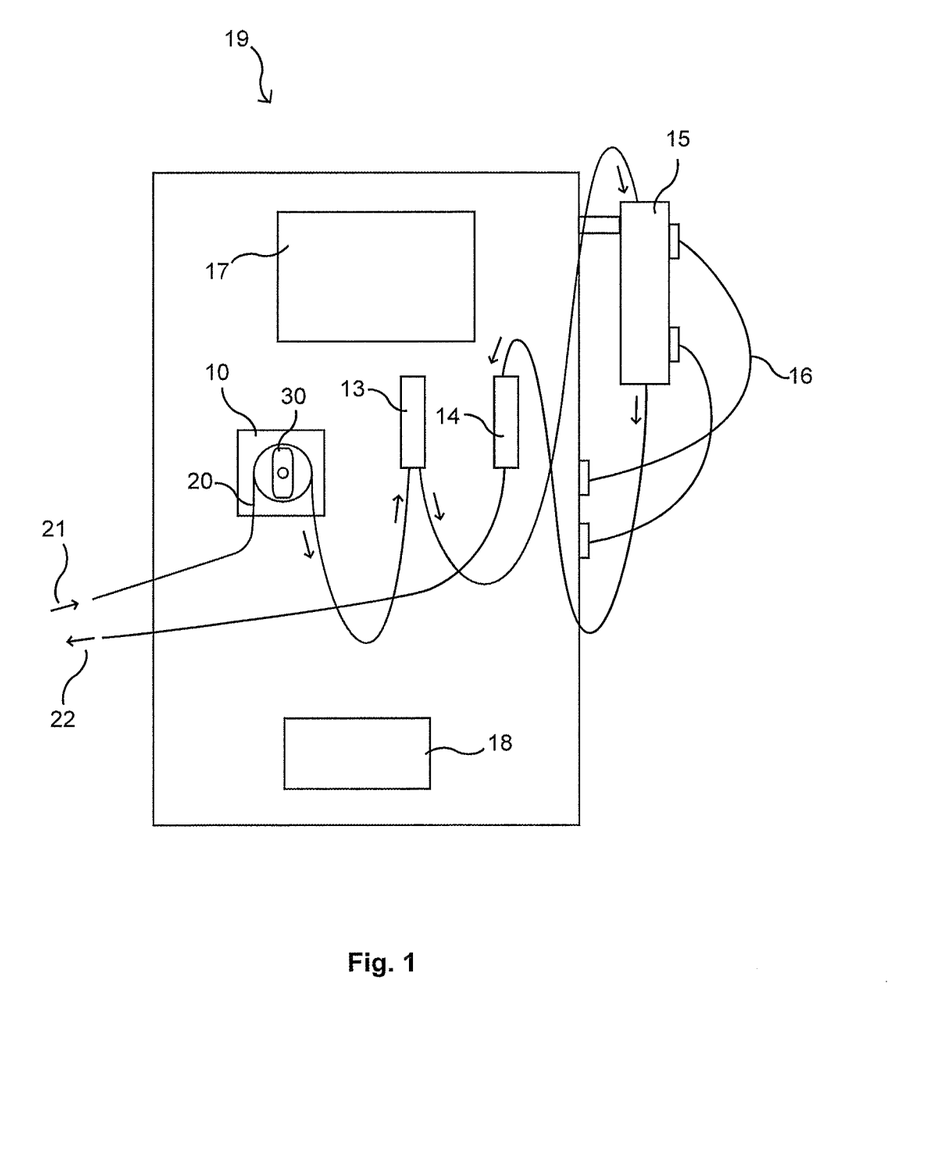
FIG. 1 a schematic illustration of a medical device for extracorporeal blood treatment with a blood pump.

FIG. 1 shows a schematic illustration of the essential basic components of a medical device 19 for extracorporeal blood treatment comprising a blood pump wherein in particular the blood pump concerns a peristaltic pump. The peristaltic pump thus comprises a pump housing 10 which typically is attached to the front side of the dialysis machine 19.

Arterial blood 21 of a patient is fed to this peristaltic pump and conducted through the extracorporeal blood circuit. Subsequently the blood is returned to the patient as venous blood 22. In this way the blood is supplied by means of the pump through a transfer system which is connected to a plurality of components of the dialysis device, wherein a tube segment 20 of the transfer system is placed in the peristaltic pump and a rotor 30 supplies the blood peristaltically through said tube segment 20, as is to be understood by the enlarged view of FIG. 2.

After passing through the blood pump, and after it may have passed though an arterial air trap 13, the blood reaches the dialyzer 15. In the dialyzer 15 the blood is cleaned by substance exchange with a dialysate 16 which is delivered to and removed from the dialyzer 15. After passing through the dialyzer 15, the blood reaches a venous air trap 14 and is then delivered to the patient. This circuit of the patient's blood is labelled with arrows in FIG. 1.

The setting of parameters of the dialysis and the monitoring of the therapy can take place via a display/input unit 17, which may be configured as a touch screen. Furthermore, the dialysis device 19 comprises a control unit 18.

Figure 2:
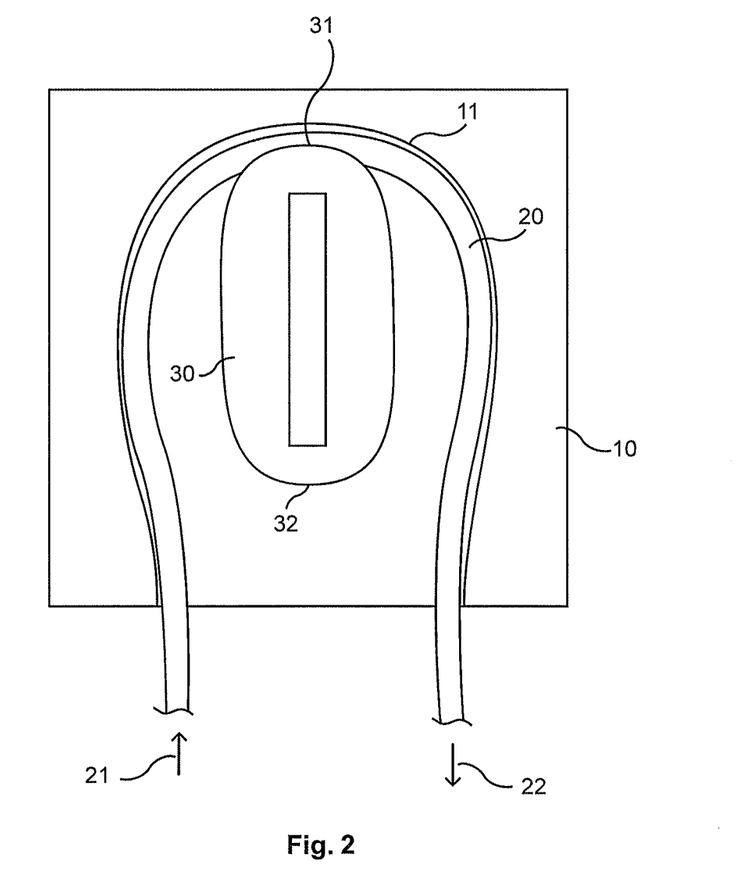
FIG. 2 a schematic illustration of a view on a peristaltic pump.

FIG. 2 shows a schematic illustration of a view on a peristaltic pump with inserted tube segment 20 and rotor 30. The peristaltic pump additionally comprises the pump housing 10, and the lid apparatus according to the invention is suited in particular to the pivotable attachment of a lid to this pump housing 10 in order to cover the peristaltic pump during the therapy, while also allowing the operator access to the transfer system 20 if required.

A curved running surface 11 is configured in the pump housing 10 by means of a recess in the pump housing 10, in which the tube segment 20 can be inserted in a looped form such that both its tube ends protrude downwardly from the pump housing 10. Thereby the recess may be configured in the pump housing 10 with a side surface which runs essentially uniformly perpendicular to the front side of the device, or the running surface 11 is formed non-uniformly by a side surface of the recess, which is concave or even twists on itself.

A rotor 30 is attached within the running surface 11, wherein the rotor for example has an elliptical circumference such that under rotation it can easily compress the tube segment 20 at its main vertices 31, 32. By turning of the rotor 30 clockwise, for example, the region of a compressed tube segment moves clockwise as well, until the corresponding main vertex releases itself again from the tube segment. In this time, the opposite lying main vertex has already remade contact with the tube segment 20, such that blood in the corresponding region of the tube segment 20 which lies in front of the region of the tube segment compressed by the rotor 30, is peristaltically supplied from the pump entry to the pump exit. Connectors can be configured or attached at both ends of the tube segment 20, wherein said connectors create a connection to further supply and discharge lines.

According to the orientation of the pump housing 10 on the medical device 19, the lid in FIG. 2 is mounted above, below, or to the side, such that it is pivotable upwards, downwards, or to the side.

Figure 3:
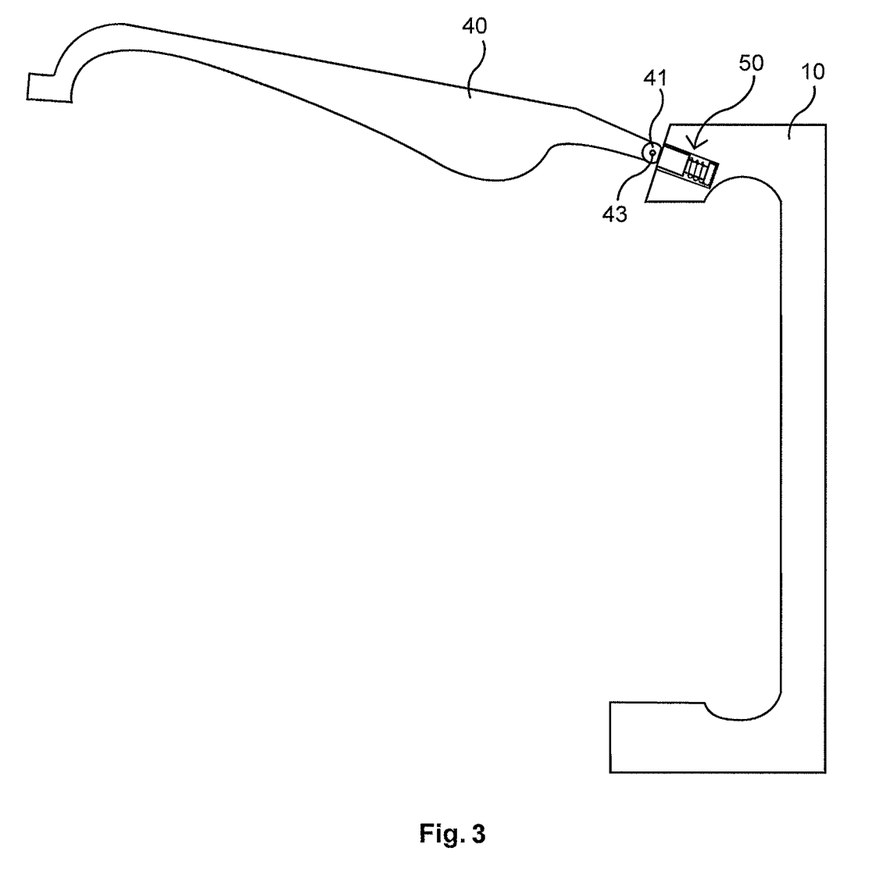
FIG. 3 a schematic side view on a peristaltic pump with opened lid.

FIG. 3 shows a schematic side view on the peristaltic pump, wherein the peristaltic pump in FIG. 2 is shown from below.

Figure 4:
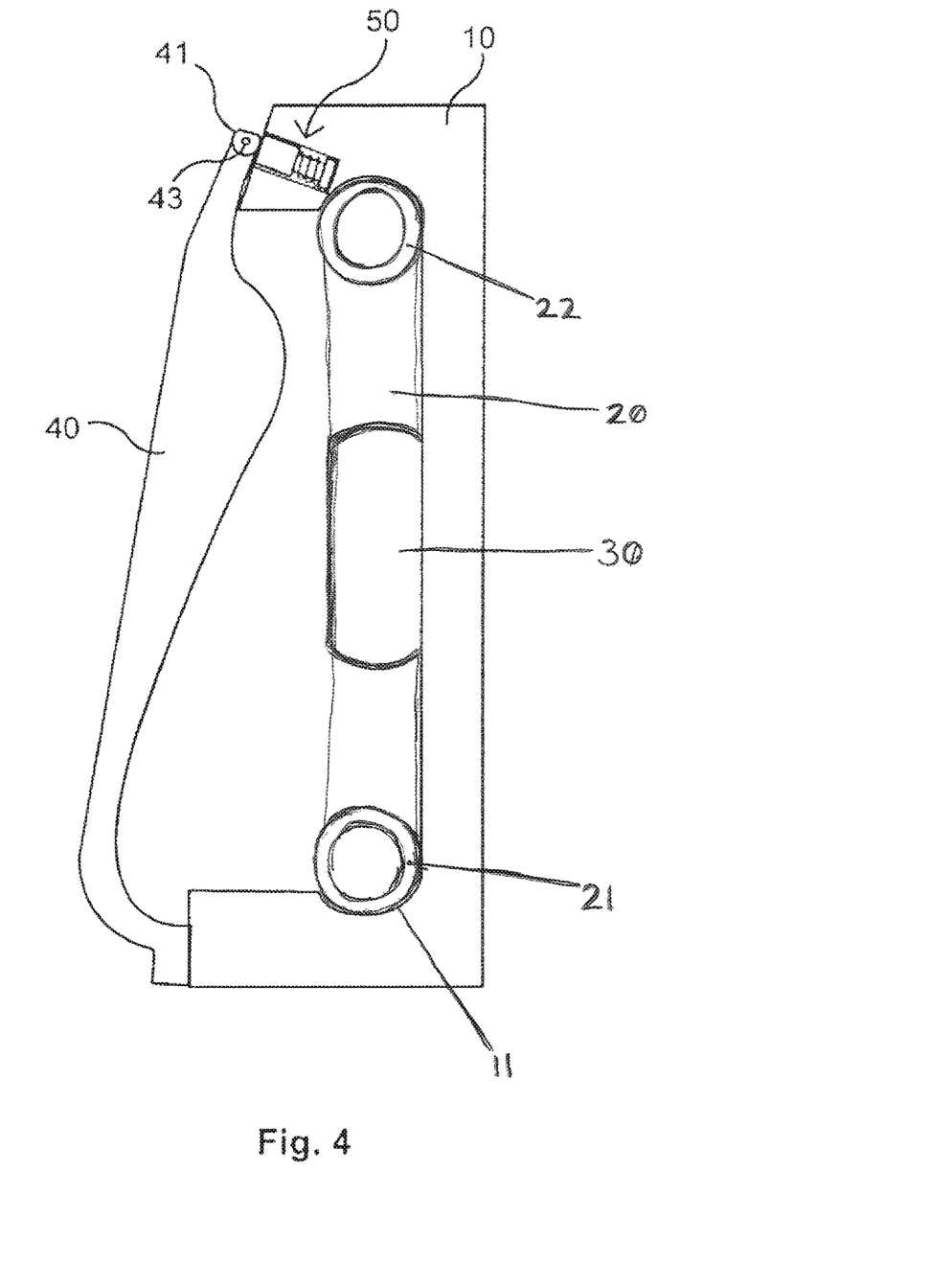
FIG. 4 a schematic side view on a peristaltic pump with closed lid.

The lid 40 may completely cover the pump housing 10 with its running surface 11 and the rotor 30 and is pivotably mounted in the upper (in FIG. 3) region of the housing 10. In addition a retention system 50 is provided which is introduced in a hole 12 (see FIGS. 5a to 5c) inside the pump housing 10. The lid 40 is rotatable relative to the retention system 50 about an axis of rotation, 43, and FIG. 3 shows the lid 40 in an opened position. FIG. 4 on the other hand shows a lid 40 in the closed position.

Figure 5A:
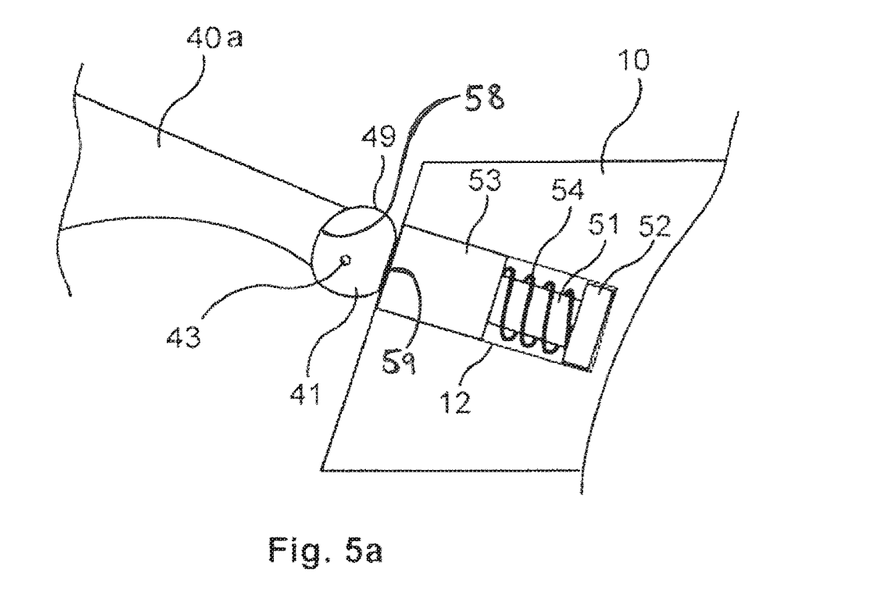
FIG. 5a an enlarged view of a retention system with opened lid.
Figure 5B:
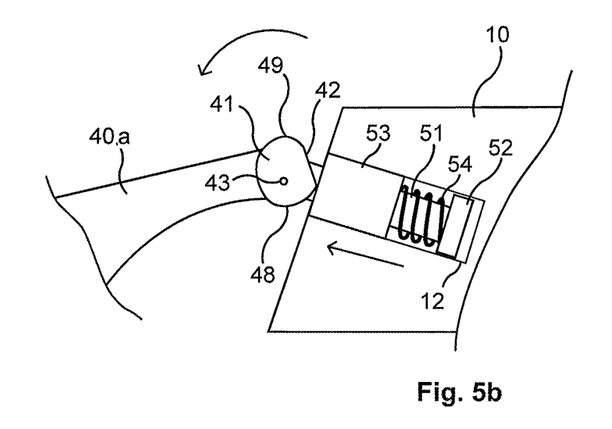
FIG. 5b a retention system according to FIG. 4b in the process of closing.
Figure 5C:
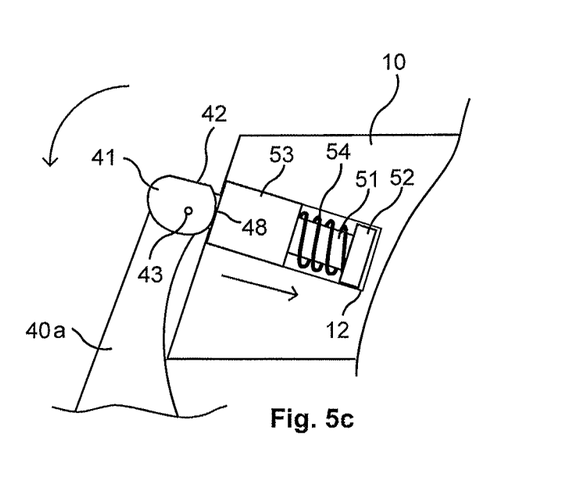
FIG. 5c a retention system according to FIG. 4b with closed lid.

The defined opened position of FIG. 3 is achieved through an interaction of the geometry of the lid 40 and the spring loaded retention system 50 of the pump housing 10. The same applies to the defined closed position of FIG. 4. To explain this in more detail, enlarged views of both these regions are shown in FIGS. 5a to 5c. FIG. 5a shows the lid 40 again in the opened position of FIG. 3. It can be seen here that the retention system 50 consists of a lid support 51, a plain bearing bush 53, a stop 52 and a spring 54. The lid support 51 is essentially cylindrically formed and comprises a plate-shaped stop 52 at the end located inside the pump housing 10. The stop 52 may however also be configured in another way, such as by protruding pins, or an end of the spring 54 is fixed to the lid support 51. A pin support in the form of a hole is provided at the opposite end of the lid support 51, to which pin support the lid 40 is attachable by means of a hinge pin. In that case the axis of rotation 43 of the lid 40 is located inside this hole.

The lid support 51 is movably guided within a plain bearing bush 53 which may be configured in the shape of a hollow cylinder. In this way the plain bearing bush 53 is firmly anchored in the pump housing 10, wherein the anchoring may be made via a press fit for example. Alternatively or in addition, an anchoring of the plain bearing bush 53 may also be made by other connection methods such as for example adhesive, pin and/or screwed connections. The cylindrically formed lid support 51 can move axially inside the fixed bush 53. A biased compression spring 54 is located between the plain bearing bush 53 and the stop 52, wherein said spring surrounds the lid support 51. The spring 54 is either further compressed or slightly relaxed, according to the direction of the movement of the lid support 51 inside the plain bearing bush 53, wherein the spring load pushes the stop 52 away from the plain bearing bush 53 and therefore pulls the lid support 51 into the plain bearing bush 53. The compression spring 54 may thereby be clamped between the plain bearing bush 53 and the stop 52 such that a constant pulling force results.

The pump lid 40 comprises, in addition to a plate-shaped lid region, with which the pump housing 10 is coverable, a joint section 40a in the region of the axis of rotation 43. The joint section 40a of the lid 40 on one side and of the lid support 51 on the other side form a pivot joint for pivoting the lid 40 relative to the pump housing 10. The joint section 40a of the lid 40 is provided with a rolling and latching geometry 41. This rolling and latching geometry 41 is essentially cylindrically formed, wherein the axis of rotation 43 of the lid 40 can however pass eccentrically through this rolling and latching geometry 41. Differently from a purely cylindrical form, the rolling and latching geometry 41 comprises at least one latching surface 42 for a latching function. This may be level and flat, or the latching surface 42 may comprise a waved or jagged outer surface. In particular a concave latching surface may be provided.

In the opened position of the lid 40, the rolling and latching geometry 41 is aligned such that the latching surface 42 bears on the plain bearing bush 53. The stop 52 is pushed away from the plain bearing bush 53 by the spring load of the spring 54, so that the lid support 51 is pulled into the plain bearing bush 53. In this way a pulling force is exerted on the lid 40, wherein the pulling force pulls the latching surface 42 to the plain bearing bush 53 and/or the housing 10. In this way the lid 40 is latched in this position and cannot pivot downwards due to gravity, to which end the spring strength is suitably selected.

However if deliberate pressure is exerted downwards (in FIG. 3) on the lid 40 by the user, the rolling and latching geometry 41 rotates in the counter clockwise sense about the axis of rotation 43. In order to be able to carry out this rotation, the lid support 51 is easily pulled out of the plain bearing bush 53 against the load of the spring, because the edge of the latching surface 42 must be overcome. This process is shown in FIG. 5b, wherein the pivoting of the lid 40 is indicated with a curved arrow, while the movement of the lid support 51 is indicated with a straight arrow. In this way, the latching of the lid 40 in the defined opened position is removed and the rolling and latching geometry 41 comprises a first convex rolling curve 48, along which the rolling and latching geometry 41 now slides against the plain bearing bush 53. Here the spring load may be selected such that the requirements for the actuation forces and the supporting force for a latching function are fulfilled.

Furthermore, the spring load may be selected such that the requirements for an automatic active closing of the lid 40 and for the holding in the closed position are also fulfilled. This closed position is shown in FIG. 5c, wherein the lid support 51 could be lightly pulled again into the plain bearing bush 53 by the spring load, and now the convex rolling curve 48 bears on the plain bearing bush 53. Here, the convex rolling curve 48 is defined and formed such that the lid 40 is held in this position. It can only be opened therefore by a significant force from below against lid 40.

FIGS. 5a and 5b show further a second convex rolling curve 49 on the rolling and latching geometry 41, wherein said convex rolling curve is formed with a second edge on the other side of the latching surface 42. If the lid 40 is pushed upwards from the latched position of FIG. 5a, the edge between latching surface 42 and the second rolling curve must also be overcome against the spring load, but the lid 40 can theoretically be pivoted further upwards. In this way an overload protection is provided.

Thus the rolling and latching geometry 41, i.e. the latching surface 42 and the rolling curves 48 and 49, forms a first contact surface 58, and the abutting surface of the plain bearing bush 53 forms a second contact surface 59 of the pair of contact surfaces according to the invention, which are pushed together by the spring load.

Figure 6:
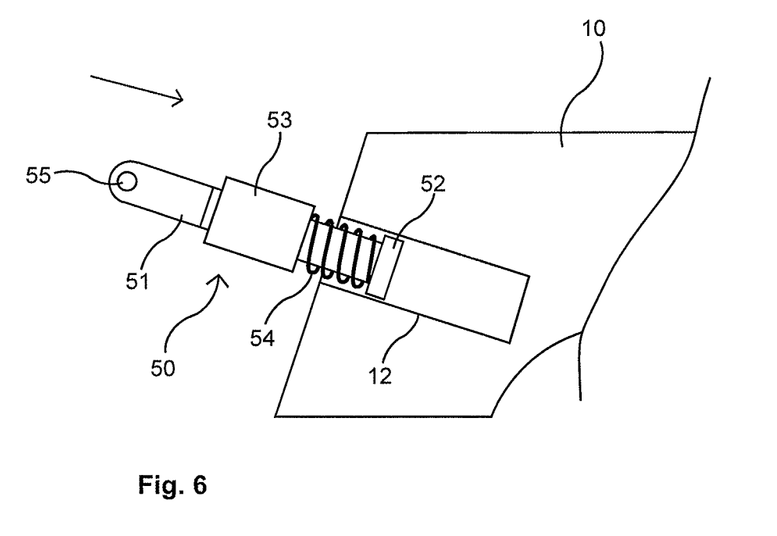
FIG. 6 a retention system during assembly to the pump housing.

FIG. 6 shows an enlarged view of the retention system during assembly to the pump housing 10. To this end a cylindrical blind hole 12 is provided in the pump housing 10, which may, however, also be a through hole. The retention system 50, consisting of the lid support 51 with the stop 52, the plain bearing bush 53 and the compression spring 54, can be pre-assembled and then inserted as a spring assembly in the hole 12. Here the stop 52 has a smaller diameter than the plain bearing bush 53 so that the stop 52 can be placed in the hole 12 before the plain bearing bush 53 is anchored, for example with a press fit into the housing 10. In the case of a through hole, the stop 52 may, together with the spring 54, also protrude out of the hole on the other side as well.

The outer contour of the plain bearing bush 53 may be cylindrically formed, but may also comprise another geometry. For example square, rectangular, oval, or polygonal cross sections may be considered, such that the cross section of the hole 12 is suited to the outer contour of the plain bearing bush 53.

A pin support in the form of a hole 55 is provided on the side of the lid support 51 opposite the stop 52. A hinge pin can be pushed through this hole 55, wherein said hinge pin connects the lid 40 with the retention system 50. The hinge pin then forms the axis of rotation 43 of the lid 40. This end region of the lid support 51, in which the pin support 55 is provided, may be cylindrically formed, as with the rest of the lid support 51. It may however also be plate-shaped such that the lid support 51 has a rectangular cross section in this region. In this way, the transition between the round and the cornered cross section may be positioned such that in operation it is located near the outer contour of the plain bearing bush 53.

Figure 7:
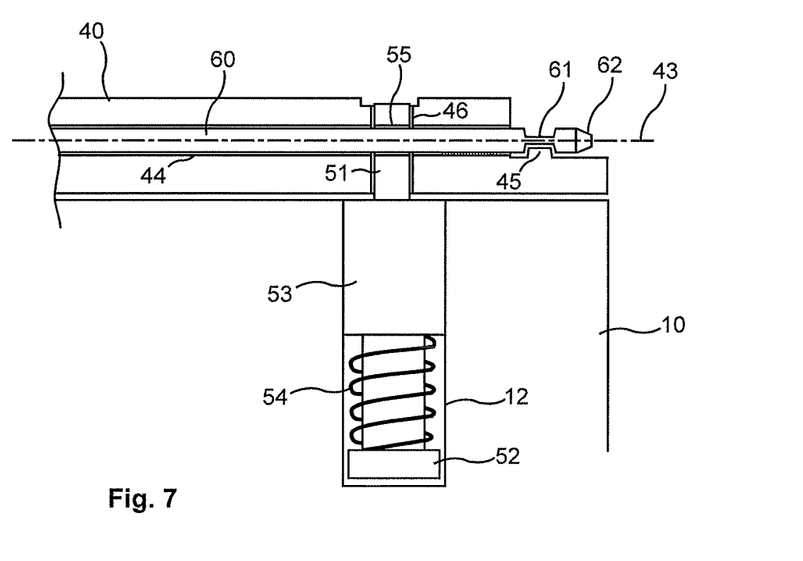
FIG. 7 a partial view of a retention system with assembled lid.

The attachment of the lid 40 to the lid support 51 is to be understood schematically from a view in FIG. 7. Here the support system 50 is anchored with the plain bearing bush 53 in the hole 12 in the pump housing 10. The lid support 51 protrudes for example with its plate-shaped section from the plain bearing bush 53 and is inserted in a hole 46 in the lid 40. This hole 46 runs transversely to the axis of rotation 43 of the lid 40. A hinge hole 44 is provided inside the lid, wherein the hinge hole runs along the axis of rotation 43. A hinge pin 60 can be pushed through this hinge hole 44, such that the hinge pin penetrates the lid support 51 in the region of the pin support 55. In this way a rotational bearing is provided in the axis of rotation 43, about which the lid 40 is pivotable, wherein a clearance fit is realised.

By this construction of the retention system 50, the plain bearing bush 53 can be fixed in the hole 12, wherein said plain bearing bush 53 can lie independent of radial position. Consequently the lid support 51 can be rotated within the plain bearing bush 53 such that the lid 40 can be mated with the hole 46 on the plate-shaped section of the lid support 51. In this position the hinge pin 60 can be introduced into the hinge hole 44 such that said hinge pin 55 penetrates the pin support 55 in the lid support 51.

To fix the hinge pin 60 within the lid 40, the hinge pin 60 comprises a circumferential groove 61. A raised portion 45 in the lid 40 engages into this groove 61, when the hinge pin is pushed from the left through the hinge hole 44. To be able to introduce the pin 60 more easily into the hole 47, the pin may be provided at its end with a circumferential chamfer 62. The hinge pin 60 is secured against sliding out from the hole 47 by means of locking with the groove 61 and the constantly acting spring load. If the region of the groove is free, then the hinge pin 60 can however be released from axial locking by gently lifting at the chamfer 62.

The invention claimed is:

1. Lid apparatus for a medical device for extracorporeal blood treatment, comprising:
    a lid hinged by means of at least one pivot joint at the medical device, wherein the pivot joint comprises a first joint section and a second joint section, wherein said joint sections are pivotable with respect to each other about an axis of rotation at least between a first position, in which the lid is open, and a second position, in which the lid covers at least a part of the medical device, wherein a relative distance between the axis of rotation and the medical device in the first position and the second position is different;
    wherein said joint sections are releasably lockable in at least one of the first position or the second position, wherein the lid apparatus comprises at least one pair of contact surfaces having a first contact surface and a second contact surface which, perpendicular to the axis of rotation, are resiliently biased against each other, wherein the first contact surface comprises a rolling and latching geometry resiliently biased against the second contact surface such that the lid latches in the second position, and the pivoting moveability of the pivot joint is only released when the resilient biasing force is overcome; and
    wherein the first contact surface comprises a flat portion having a first edge and a second edge, a first curved portion adjacent the first edge, and a second curved portion adjacent the second edge, and wherein the axis of rotation is closer to the second contact surface when at least one of the first or second curved portion is in contact with the second contact surface than when the flat portion is in contact with the second contact surface.

2. Lid apparatus according to claim 1, wherein the lid is pivotably mounted about the axis of rotation at a spring loaded lid support, wherein a constant pulling force is applied to the lid by the spring loaded lid support.

3. Lid apparatus according to claim 2, wherein the medical device comprises a housing section having at least one retention system including the spring loaded lid support, the spring loaded lid support comprising at least one of a pin or cylindrically shaped lid support, section, which is movable with respect to the medical device under load of a spring; the first contact surface comprising the rolling and latching geometry is configured at the first joint section positioned at the lid; and the flat portion of the first contact surface is a latching surface; and at least one of the first or second curved portion is a convex rolling curve, wherein
    when the lid latches in the second position, the latching surface bears on the second contact surface of the pair of contact surfaces, while, upon pivoting of the lid, the rolling curve of at least one of the first or second curved portion slides from the second position along the second contact surface of the pair of contact surfaces.

4. Lid apparatus according to claim 1, wherein, the retention system includes a plain bearing bush within which a spring loaded lid support is axially movably mounted, wherein the plain bearing bush is fixed in a housing section of the medical device.

5. Lid apparatus according to claim 4, wherein the spring loaded lid support protrudes from the plain bearing bush with two ends lying opposite each other, wherein a bearing for the lid is configured at one end, while at the other end the spring loaded lid support comprises a stop, and the retention system further includes a compression spring which surrounds the spring loaded lid support and is biased between the stop and the plain bearing bush.

6. Lid apparatus according to claim 4, wherein the second contact surface of the pair of contact surfaces is configured at the plain bearing bush, the flat portion of the first contact surface is a latching surface which bears on the plain bearing bush when the lid is in the second position, and the at least one of the first or second curved portion, upon pivoting of the lid, slides from the second position along the plain bearing bush.

7. Lid apparatus according to claim 1, wherein the flat portion of the first contact surface is disposed between the first curved portion and the second curved portion.

8. Lid apparatus according to claim 1, wherein a hinge hole is provided in the first joint section of the lid, through which the axis of rotation passes, and that at least one second hole passes transversely through said hinge hole, wherein a spring loaded lid support is inserted in the second hole such that a pin support of the spring loaded lid support lies inside the hinge hole and is penetrated by a hinge pin, wherein the hinge pin is inserted in the hinge hole.

9. Medical device for extracorporeal blood treatment, including a lid apparatus according to claim 1.

10. Medical device according to claim 9, comprising at least one peristaltic pump having a pump housing which comprises a curved running surface and a rotor that rotates inside the running surface, wherein a tube segment of an extracorporeal blood circuit is introduceable between the running surface and the rotor, and the peristaltic pump includes the lid apparatus, wherein the pump housing is at least partially coverable by the lid in a closed position.

* * * * *